United States Patent
Cristoni et al.

(10) Patent No.: US 9,816,980 B2
(45) Date of Patent: Nov. 14, 2017

(54) APPARATUS AND CORRESPONDING METHOD FOR SAMPLING AND ANALYZING DRUGS AND RESPECTIVE METABOLITES IN BREATH AIR, PARTICULARLY SUITABLE FOR PERFORMING ROAD DRUG TESTS

(71) Applicants: Simone Cristoni, Vanzago (MI) (IT);
Rosario Billetta, Del Mar, CA (US);
Claudio Giuliani, Pogliano Milanese (IT)

(72) Inventors: Simone Cristoni, Vanzago (IT);
Rosario Billetta, Del Mar, CA (US)

(73) Assignees: Simone Cristoni, Vanzago (IT);
Rosario Billetta, Del Mar, CA (US);
Claudio Giuliani, Pogliano Milanese (IT)

(*) Notice: Subject to any disclaimer, the term of this patent is extended or adjusted under 35 U.S.C. 154(b) by 0 days.

(21) Appl. No.: 14/777,818

(22) PCT Filed: Mar. 17, 2014

(86) PCT No.: PCT/EP2014/055277
§ 371 (c)(1),
(2) Date: Sep. 17, 2015

(87) PCT Pub. No.: WO2014/147015
PCT Pub. Date: Sep. 25, 2014

(65) Prior Publication Data
US 2016/0299125 A1    Oct. 13, 2016

(30) Foreign Application Priority Data
Mar. 18, 2013 (EP) .................................. 13159744

(51) Int. Cl.
*G01N 33/497* (2006.01)
*A61B 5/097* (2006.01)
(Continued)

(52) U.S. Cl.
CPC ........... *G01N 33/497* (2013.01); *A61B 5/097* (2013.01); *G01N 1/2205* (2013.01);
(Continued)

(58) Field of Classification Search
CPC ............. G01N 33/497; G01N 33/4972; G01N 2001/2244; A61B 5/097
See application file for complete search history.

(56) References Cited

U.S. PATENT DOCUMENTS 5,425,374 A * 6/1995 Ueda .................... G01N 33/497
422/84
5,834,626 A    11/1998 De Castro et al.

FOREIGN PATENT DOCUMENTS

EP    2 518 499 A1    10/2012
GB    2 295 679 A     6/1996

OTHER PUBLICATIONS

International Search Report, dated May 6, 2014, from corresponding PCT application.

* cited by examiner

*Primary Examiner* — Paul West
(74) *Attorney, Agent, or Firm* — Young & Thompson

(57) ABSTRACT

A portable apparatus to sample and analyze volatile organic compounds in breath air, includes:
a box internally divided in two internal sections, each housing a sample collecting tube or filter in turn containing a stationary phase suitable for retaining determined analytes, as drugs and/or respective metabolites, having specific chemical physical properties, contained in breath air;

(Continued)

a pre-accumulation chamber for receiving breath air from the outside through a breath entrance connection and for feeding the received breath air to the sample collecting filters housed in the two sections, with these two sample collecting filters being connected in parallel to the chamber; and a tool application kit for removing the two sample collecting filters from the respective sections in the box of the apparatus, in a way that avoids any contamination thereof, and for extracting the analytes that are retained by the stationary phase on the same two sample collecting filters.

12 Claims, 3 Drawing Sheets

(51) Int. Cl.
  *G01N 1/22* (2006.01)
  *G01N 30/72* (2006.01)
(52) U.S. Cl.
  CPC ..... *G01N 30/7206* (2013.01); *G01N 30/7233* (2013.01); *G01N 33/4972* (2013.01)

APPARATUS AND CORRESPONDING METHOD FOR SAMPLING AND ANALYZING DRUGS AND RESPECTIVE METABOLITES IN BREATH AIR, PARTICULARLY SUITABLE FOR PERFORMING ROAD DRUG TESTS

FIELD OF THE INVENTION

The inventions relates to an apparatus and a corresponding method, based on breath air analysis, to collect and analyze road drugs, also synthetically called Breath Analysis Collecting Tool (BACT).

In particular the invention provides an innovative apparatus or device suitable for simultaneously collecting two samples of the same air that is breathed out by a person, wherein the former sample is used to perform a drug test for detecting the presence of drugs in the breath air of the person and thereby verify if he is under the effect of drugs, the latter sample is used to confirm the presence of drugs and analyze the respective metabolites, whereas this drug presence was positively detected from the results of the drug test.

The apparatus of the invention is also designed to avoid contaminations and ensure the traceability of the samples that are used to conduct the drug test and verify its result, as requested by government rules and namely by police, which is usually entrusted with performing the drug tests on the road.

BACKGROUND OF THE INVENTION AND RELATED STUDIES

Road drugs also usually called street drugs are a serious social problem (see Singer M. Int J Drug Policy. 2008 December; 19(6):467-78), in that the abuse of road drugs not only leads to dependence and to serious diseases in the addicts, but it can lead to relevant risks in the community.

For instance, the number of road accidents due to drug assumption from drivers is dramatically increased in the recent years (Penning R. et al. Curr Drug Abuse Rev. 2010 March; 3(1):23-32). In particular, road-side studies indicate that 1-15% of drivers drive under the influence of one or more drugs of abuse. Indeed, after drug use, drivers do more often cause accidents than non-users.

Information on drugs and traffic safety comes from road-side studies, epidemiological research, experimental studies on driving-related skills, and on-the-road effective driving tests. Road-side studies show that drivers most frequently result positive to drug tests following the abuse of alcohol and/or cannabis.

Thus, the police force needs for a simple and effective test to quickly and selectively detect road drugs in drug addicts.

Actually, different apparatuses and tests have been developed for detecting the presence of drugs and validating this presence in biological fluids, for many purposes and for being applied on many categories of persons like drivers or jailed persons, etc. (Maurer H H. Anal Bioanal Chem. 2009 January; 393(1):97-107, Jaffee W B et al. J Subst Abuse Treat. 2007 July; 33(1):33-42, Schuckman H. et al. Subst Use Misuse. 2008; 43(5):589-95).

Some apparatuses are based on biochemical tests (Schuckman H. et al. Subst Use Misuse. 2008; 43(5):589-95).

These approaches are mainly suitable for performing drug tests both in the road and in the specialized centers for checking drugs in the addicts (hospitals, forensic medicine institutions etc).

Mass spectrometry technology, in its different configurations (e.g.: Gas Chromatography-Mass Spectrometry (GC-MS), or Liquid Chromatography-Mass Spectrometry (LC-MS)), is widely used for validating and confirming the results of the drug tests that are used for detecting the presence of road drugs in a person (Maurer H H. Anal Bioanal Chem. 2009 January; 393(1):97-107).

In particular different applications have been developed for validating the presence of drugs and determining the respective amounts in various biological fluids like urine (Allen K R. Ann Clin Biochem. 2011 November; 48(Pt 6):531-41), blood (Moeller M R. The Drug Monit. 2002 April; 24(2):210-21), hair (Cooper G A Ann Clin Biochem. 2011 November; 48(Pt 6):516-30), skin (Levisky J A. et al. Forensic Sci Int. 2000 May 8; 110(1):35-46) and oral fluids (Allen K R. Ann Clin Biochem. 2011 November; 48(Pt 6):531-41, Schramm W. et al. J Anal Toxicol. 1992 January-February; 16(1):1-9).

An increasing number of toxicology laboratories are choosing to expand the services they offer to include hair testing in response to customer demands.

In fact hair provides the toxicologist with many advantages over conventional matrices in that it is easy to collect, is a robust and stable matrix that does not require refrigeration, and most importantly hair provides a historical profile of the exposure of an individual to drugs or analytes of interest.

The establishment of hair as a complementary technique in forensic toxicology is a direct result of the success of the matrix in medical legal cases and of the availability of a wide range of applications.

However, before introducing hair testing, laboratories must consider what additional requirements, that extend beyond the simple adaptation of known and validated methodologies for blood or urine, the laboratories will need to respect in order to effectively implement in the practice this hair testing.

The effective implementation of hair testing implies many challenges that are to be overcome, as the lack of control on the quality of the materials, the extensive protocols for handling the samples, and the low drug concentration in the hair thereby requiring a greater instrumental sensitivity for detecting the drug.

Moreover hair testing appears to be not optimal in order to control and check the abuse of road drugs from drivers.

This is essentially due to the fact that a positive result, as obtained by hair testing, does not demonstrate that the driver was necessarily under the drug effect.

In fact the road drug assumption might be occurred many days before the hair sampling and test time.

Thus, it is not possible to demonstrate that the person was under the drug effect when the test was performed on him, whereby the authorities cannot incriminate the checked person even if he resulted really positive according to the hair testing.

The same problem is also present in urine analysis that is a good checking test but not efficiently usable to demonstrate that the person is under the road drug effect.

The main biological fluid used and legally recognized from the authorities to demonstrate that drivers are under road drug effect is blood (Moeller M R. The Drug Monit. 2002 April; 24(2):210-21).

In many countries Immunochemical and Gas chromatography-mass spectrometry (GC-MS) are still the state-of-the-art techniques for checking the presence of drugs in a person, while Liquid chromatography-tandem mass spectrometry (LC-MS/MS) is used to confirm the drugs assumption.

A promising and interesting new strategy and technique for detecting the assumption of road drugs from drivers is the so-called breath analysis or breath air analysis.

In particular different methodologies and applications, based on breath analysis, have been recently developed, wherein breath analysis is associated with mass spectrometry.

In fact, breath air is in contact with lung and related blood circulation, whereby an exchange of substances takes place between the air in the lung and the blood.

Thus, road drugs and related metabolites, when detected in the breathed out air, confirm that the same are present in blood and that the person is under the drug effect.

A device for sampling Δ9-Tetrahydrocannabinol (THC) and its acid metabolite (THCCOOH) in breath has been recently studied and developed by the group of Beck (Beck et al. Journal of Analytical Toxicology, Vol. 35, October 2011).

In this study, breathed out air was sampled from 10 regular cannabis consumers and conveyed by suction through an Empore C 18 disk in order to retain the analytes of interest contained in the sample of air.

Then the analytes were extracted from the disk with hexane/ethyl acetate, and the resulting extract was evaporated, so as to gain dryness, and successively again dissolved in 100 μL of hexane/ethyl acetate.

Finally a rate of 3 μL of this solution was injected into the LC-MS-MS system and analyzed using positive electrospray ionization and selected reaction monitoring.

In the samples collected 1-12 hours after cannabis smoking, tetrahydrocannabinol was detected in all 10 persons.

The rate of excretion was between 9.0 and 77.3 pg/min. Identification of tetrahydrocannabinol was based on correct retention time relative to tetrahydrocannabinol-d(3) and correct product ion ratio.

In three samples, peaks were observed for tetrahydrocannabinol carboxylic acid, but these did not fulfill identification criteria.

Still, neither tetrahydrocannabinol nor tetrahydrocannabinol carboxylic acid was detected in the controls.

However, despite of the high quality of the results obtained by the authors, the above developed device, based on breath analysis, does not fit well for the control and validation tests, on the abuse of road drugs, that have to be performed by the police.

In fact, in the sampling and control procedure of the police when executing road drug tests, the following two points are essential and must be carefully considered:

a) two samples of the same breathed out air must be collected: the former to be used for checking the presence of drugs in the person that is subject to the drug test, and the latter to be used for purposes of validation and confirmation of this drug presence, whereas resulting from the former sample;

b) the traceability of the collection, storage and transportation of the sample must be always warranted, so as to certify that the sample has not been counterfeited before being subject to the instrumental analysis.

Briefly, at present there is a need for an apparatus or device, specifically based on breath analysis and adapted to be used to collect, sample and analyze drugs and the respective metabolites, that is designed and structured both for executing drug control and check-up tests, and for confirming the results of the drug control tests, so as in particular to be suitable for meeting the requirements of the police for performing road drug tests.

In the prior art there are also mentioned patent documents U.S. Pat. No. 5,834,626 A and EP 2 518 499 A1 which disclose portable devices for drug detection from exhaled breath.

However also these known devices appear to request further improvements in order to meet the above requirements, including in particular the confirmation of the results of the drug control tests.

SUMMARY OF THE INVENTION AND IMPROVEMENTS OVER THE PRIOR ART

The present invention firstly aims to fill the above lack in the prior art and to provide an apparatus or device, to be used to sample and analyze volatile organic compounds (VOCS) in breath air, that is capable of satisfying the requirements of the police for making control and validation tests on the abuse of road drugs.

The aforementioned aim can be considered completely fulfilled by the apparatus or device for sampling and analyzing volatile organic compounds in breath air, having the features defined by the independent claim 1, and by the corresponding method as defined by the independent claim 30.

Particular embodiments of the present invention are defined by the dependent claims.

BRIEF DESCRIPTION OF THE DRAWINGS

These and other objects, features and advantages of the present invention will be made clear and evident by the following description of one of its preferred embodiments, given by way of a non-limiting example with reference to the accompanying drawings, wherein.

time acquisition time: 2 minutes;
carrier gas flow rate under slit conditions (split ratio 1:20): 1 µL/min;
injection into the GC/MS instrumentation of 2 µL of the sample extracted by means of the apparatus of the invention.

DESCRIPTION OF A PREFERRED EMBODIMENT OF THE INVENTION AND OF SOME APPLICATION EXAMPLES THEREOF

Figure 1:
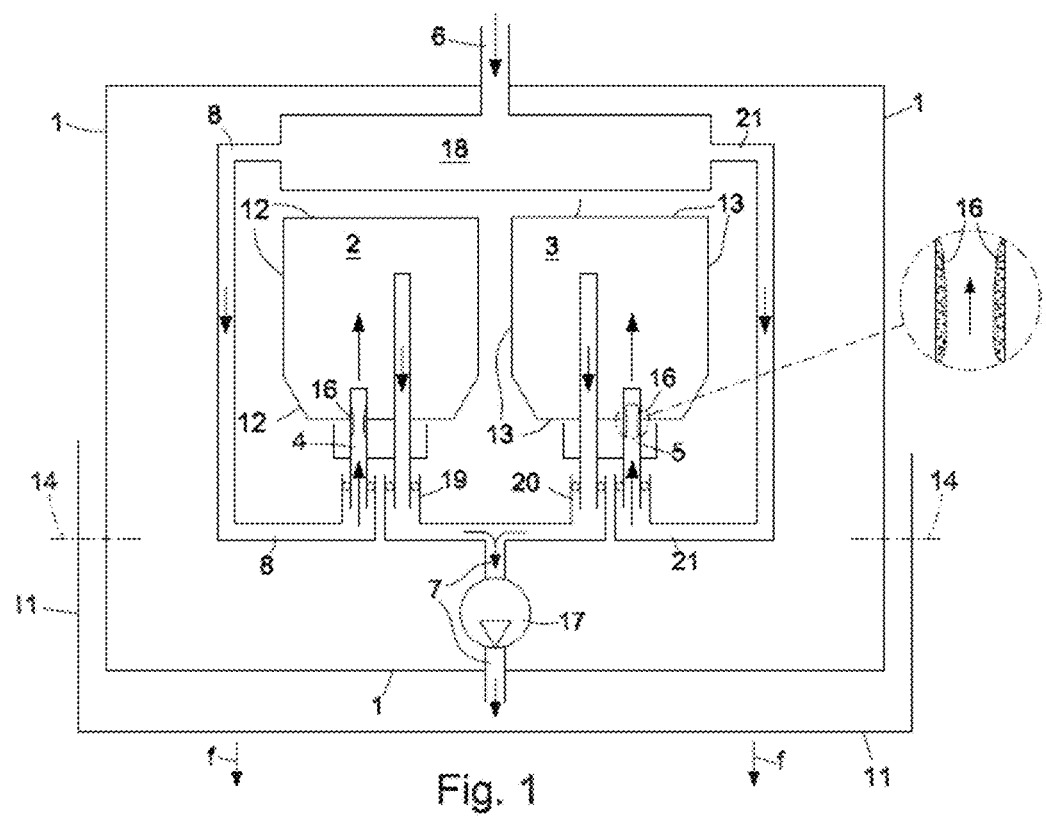
FIG. 1 is a scheme of a sampling and analyzing device or apparatus, according to the invention, for use to sample and analyze volatile organic compounds (VOCS) in breath air, thereby also called Breath Analysis Collecting Tool (BACT), in particular including a box that is internally divided into two sections each housing and containing a respective collecting filter, in the form of a tube, for retaining specific analytes of interest present in the breath air.
Figure 2:
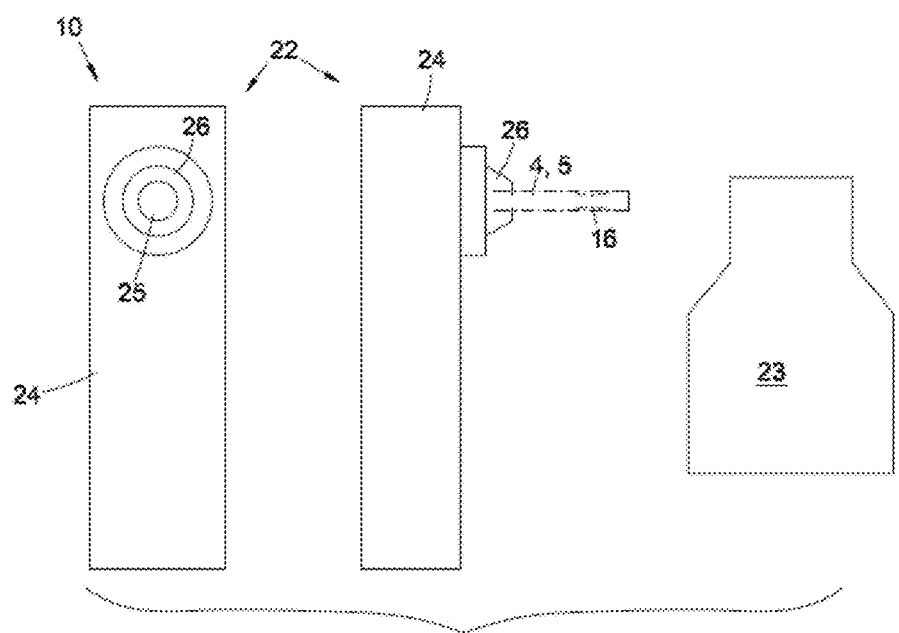
FIG. 2 is a scheme of a tool application Kit which is included in the BACT sampling and analyzing apparatus of the invention and is provided both for removing, while avoiding any contamination, the collecting filters from the box of the apparatus of FIG. 1, and for checking the presence of drugs in the same collecting filters.
Figure 3:
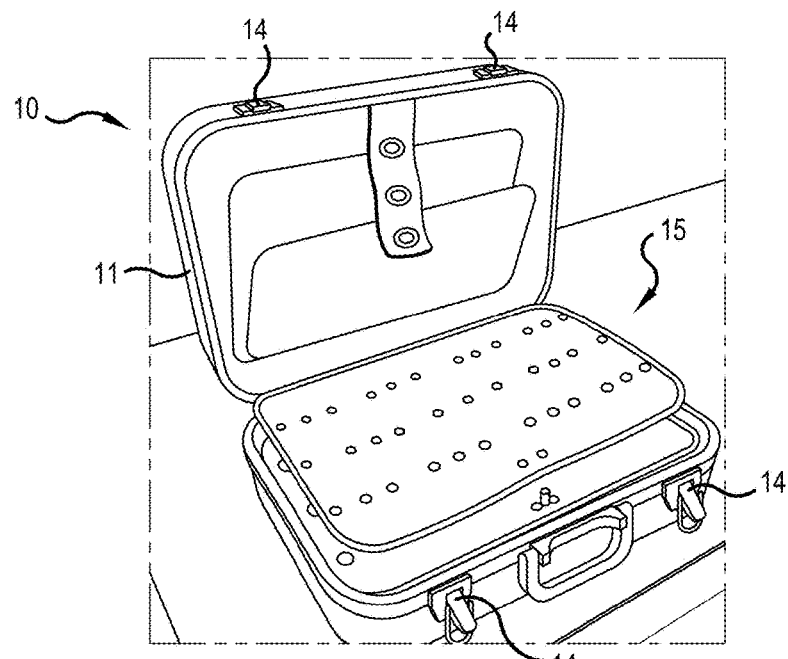
FIG. 3 is a photo of an effective exemplary of the BACT sampling apparatus of the invention of FIG. 1.
Figure 4A:
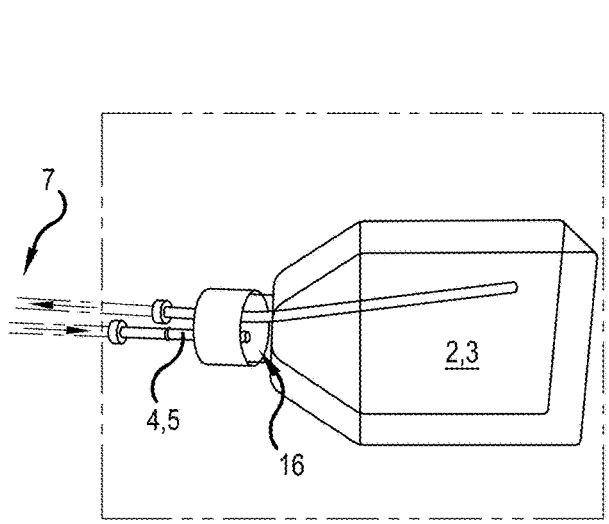
FIGS. 4A, 4B and 4C are photos of effective essential parts, as the collecting filter and the section containing it, of the BACT apparatus of the invention of FIG. 1.
Figure 4B:
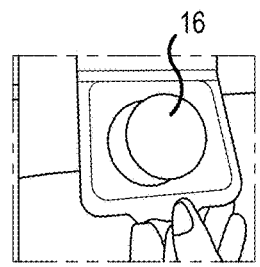
Figure 4C:
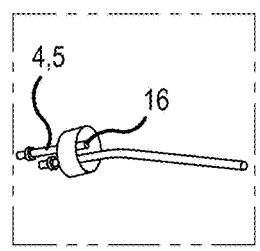

An apparatus or device of the invention, for use to sample and analyze volatile organic compounds (VOCS) in breath air, also named Breath Analysis Collecting Tool (BACT), is schematically shown in FIGS. 1 and 2, where it is generically indicated with 10.

It is a portable apparatus and is composed of an external box 1 that is internally divided into two sections indicated respectively with 2 and 3.

Each of these sections 1 and 2 houses and contains a respective sample collecting filter 4 and 5, in the form of a tube, in turn containing a chromatographic resin or stationary phase 16 that is fixed on the internal surface of the tube through covalent interaction.

This chromatographic resin 16 is suitable for retaining determined analytes having specific chemical physical properties mainly in terms of polarity, molecule dimension, molecule affinity etc.

As shown in FIG. 1, the filters or tubes 4 and 5 are connected to the external, at one side of the box 1, through a breath entrance connection 6 and a breath accumulating pre-chamber 18, and, at another side of the box 1, through a first expulsion connector 19 and a second expulsion connector 20 that are both connected to a final breath expulsion connector 7.

The pre-chamber 18 allows an accumulation of breath air obtained with different breaths.

Tubes 8 and 21 are provided for connecting the pre chamber 18 respectively with the sample collecting filters 4 and 5, housed respectively in the sections 2 and 3, whereby a parallel connection is realized between the tube 4 and 5, as shown in FIG. 1.

Means, preferably but not exclusively in the form of a pump 17, are provided for moving the breath air from the accumulator pre-chamber 18 so as to pass through the sample collecting filters 4 and 5.

In particular the pump 17 is connected to the tube 7 and is activated to pump the breath air from the accumulator pre-chamber 18 through the sample collecting filters 4 and 5, thereby making possible to retain the air analyte of interest on the sample collecting filters 4 and 5.

The pump 17 also regulates and maintains constant the breath sample flow, so as to permit an accurate and reproducible collection of the breath containing the analyte.

Moreover the pump 17 can operate at different flow rate ranging from 0,1 to 10 L/min, with the best preferred flow ratio being selected between 1 and 5 L/min.

A cover 11 is fixed by respective fixing means 14 to the box 1, so as to cover it, as schematized in FIG. 1.

In particular the cover 11 can be opened and removed from the box 1 to collect the samples, as described in the following.

The sections 2 and 3 are externally closed with two respective thin films 12 and 13 of plastic.

As it will be clear from the following, these components and means 11, 12, 13 and 14 are essential in order to ensure that the two sections 2 and 3 and the two sample collecting filters 4 and 5 housed in them have been manipulated only by authorized authorities personal.

The portable apparatus 10 of the invention also comprises a kit, generically indicated with 15 (FIG. 2) and also called BACT application kit, that is composed of a mechanical tool or instrument 22, to be used for removing the filters 4 e 5 from the respective chambers 2 and 3 in the box 1 in such a way to avoid any filter contaminations, and of an analyte extraction solution 23, to be used for extracting the analytes retained by the stationary phase 16 contained in the two sample collecting filters or tubes 4, 5, as described more in detail in the following.

The mechanical tool or instrument 22 is in turn constituted by a mechanical handle 24 that has a central stuffing 25.

In the use of the apparatus 10 of the invention, at first, with the box 1 closed by the respective cover 11, the pre-accumulation chamber 18 is filled by breath air or by vapor originating from a solution.

Moreover the rotary pump 17 is activated in order to feed the vapor or the breath air from the chamber 18 to the internal sections 2 and 3 of the box 1.

In this way, the vapor or the breath air coming from the pre-accumulation chamber 18 passes through the filters 4 and 5, and consequently the drugs and the analytes of interest contained in the vapor or the breath air are retained by the stationary phase 16 provided in the same filters 4 and 5.

In particular Δ9-Tetrahydrocannabinol (THC) or other volatile organic compounds (VOCS) of interest are retained in the filters 4 and 5.

Therefore, at this point, the analytes of interest retained by the stationary phase 16 in the filters 4 and 5 can be extracted and analyzed by means of the application kit 15.

More in detail, after having disconnected and removed the cover 11 from the box 1 of the apparatus 10, a first one of the two filters 4 and 5, for instance the filter 4, is extracted and removed from the respective section 2 in the box 1, by using the mechanical tool 22 of the BACT application kit 15.

To this purpose, the central stuffing 25 of the handle 24 of the mechanical tool 22 is pushed against the filter 4, while a crown 26 of the mechanical handle 24 removes the material of the peripheral regions around the filter 4, which thereby is retained by this stuffing 25 in the mechanical handle 24.

Then the mechanical handle 24 retaining the removed filter 4 can be hanged, or placed in some way in a storing device.

Successively the stuffing 25 can be pushed again against the filter 4, so as to release it from the mechanical handle 24 or the storing device, in order to analyze the filter 4 always by using by means of the BACT application kit 15.

In particular, in this analyzing phase, the filter 4 is washed by means of the analyte extraction solution 23 that is included in the application kit 15, so as to extract the analytes retained on the same filter 4 by the stationary phase or chromatographic resin 16.

Therefore the solution 23 can be used to verify and detect the presence or less of road or street drugs and the respective metabolites in the analytes extracted by it.

In particular, to this purpose, 2 µL of the solution obtained by washing the filter 4 and containing the extracted analytes is injected, for being analyzed, into a portable Mass Spectrometry system (MS).

The solvent of the solution 23, provided in the BACT application kit 15, that is used for extracting the analytes retained by the stationary phase 16 in the filter 4 or also the filter 5, can be chosen among H2O, H2O salts buffers, CH3CN, CH3OH depending on the road drug to be analyzed.

In particular the extraction polar solvent of this solution 23, included in the BACT application kit 15, is named Reagent A.

In the event of positive detection, by this analysis, of drug in the first filter 4, the box 1 is closed by newly fixing to it the respective cover 11, by means of the fixing means 14.

Then the box 1, closed, containing the second closed section 3 with the respective second filter 5, is sent to a qualified center (e.g. hospital, private laboratory, etc.), where the second filter 5 is analyzed through the well consolidated Gas Chromatography-Mass Spectrometry (GC-MS) or Liquid Chromatography-Mass Spectrometry (LC-MS) technologies in order to confirm the drug data that were obtained by checking the first filter 4.

EXAMPLE

For completeness, in the following there is described an example of analysis, by means of the GC-MS (Gas Chromatography-Mass Spectrometry) technique, of acetone, in turn collected from a flask and prepared for being analyzed with this GS-MS technique by using the BACT apparatus 10 of the invention.

At first, before the analysis, pure acetone is diluted 20 times using methanol.

Then the pre-accumulation chamber 18 in the box 1 is filled with vapor of the acetone solution by means of the rotary pump 17, that pumps the acetone solution vapor from the flask to the same pre-accumulation chamber 18.

The same rotary pump 17 pumps and directs the vapor from the chamber 18 to the filters 4 and 5, where the acetone and its metabolites are retained by the stationary phase 16.

Then the filter 4 or 5, retaining the acetone and its metabolites, is extracted from the box 1 by means of the mechanical tool 22 of the application kit 15 and washed by means of the analyte extraction solution 23 that is part of the same application kit 15.

In this phase, the thermal isocratic condition is: 100° C. as dilution temperature with a flow rate of 1 mL/min.

Successively 1 microliter of the solution, thus obtained by washing the filter 4 or the filter 5, is injected into the Chromatograph-Mass Spectrometer instrument, so as to be analyzed.

Figure 6:
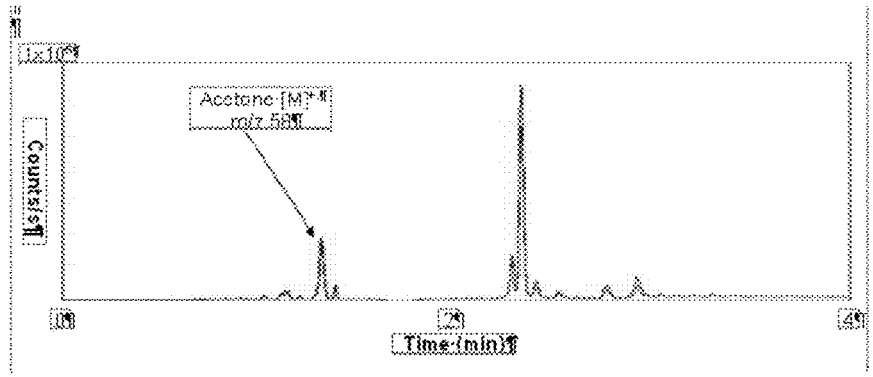
FIG. 6 is a GC/MS (Gas Chromatographic-Mass Spectrometry) chromatogram that was obtained by analyzing acetone, in turn sampled by means of the BACT apparatus of the invention, wherein the chromatogram was carried out in the following conditions.

The mass chromatogram of FIG. 6 shows the results achieved by this analysis.

In particular, as shown by this FIG. 6, a clear acetone chromatographic peak obtained by monitoring the [M].+ ion was detected with a S/N ratio of 50.

It is therefore clear, from what is described and the annexed drawings that the present invention fully achieves the objects that had been set and provides a new apparatus or device and a corresponding method, based on breath analysis, that are suitable for collecting breathed out air samples and are capable of meeting the requirements of the police for executing tests on the assumption of road drugs from drivers and for confirming the results of the tests.

In particular the apparatus or device of the invention has been designed in order to be capable of complying with the following points:

i) to simultaneously collect two breath samples: the former being used for performing a control drug test, and the latter for confirming the results of the drug control test;

j) to ensure full and complete traceability of the collection, storage and transportation of the sample, in particular as requested by the police procedures, so as to certify that the sample have not been counterfeited or falsified before being subject to the instrumental analysis.

Concerning the point i), it has been satisfied, as before described, by providing two C18 filters, connected in parallel, in the sample box 1, whereby the same breath air passes through both filters 4 and 5 and the road drugs are retained by both these filters.

Moreover the two filters 4 and are inserted in two different sub-sections 2 and 3 of the main box 1 (see FIG. 1).

A first one, for instance that indicated with 4, of the two filters 4 and 5 that interact with breath air and retain road drugs is used in order to check the presence of drugs in the collected breath air sample.

In particular, after the sample collection, this first filter 4 is treated according to a procedure which uses the material enclosed in the BACT application kit 15 (FIG. 2), in particular comprising the extraction solution 23 that is typically a solvent suitable for extracting the road drugs and the respective analytes from the first filter 4.

Figure 5:
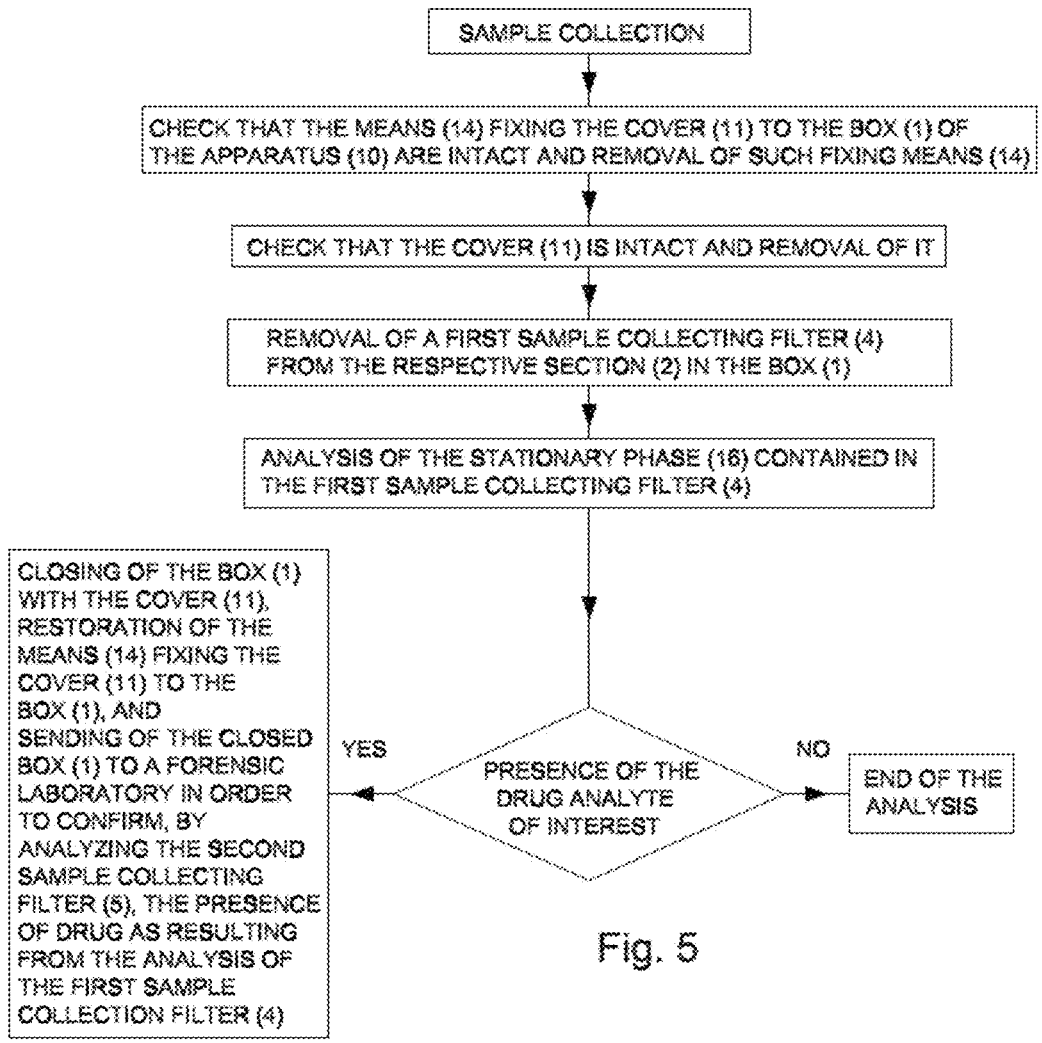
FIG. 5 is a flow chart which illustrates the use of the BACT sampling apparatus of the invention of FIGS. 1 and 2, in particular in order to guarantee the traceability of the samples during their collection, storage and transportation.

Concerning point j), reference is made to FIG. 5 of the drawings showing a flow diagram of the operative procedure, after the sample collection, that have been studied in order to guarantee the traceability of the collection, storage and transportation of the sample and thereby comply with the police procedures.

At first, the police office makes a check so as to be sure that the connector 14 of the cover 11 to the box 1 and the cover 11 are intact and not corrupted before the start of the analysis.

Then the checked person is invited to emit his breath in the entrance connection 6 of the box 1 of the apparatus 10. In this phase the pump 17 of the apparatus 10 is activated, whereby the breath air emitted by the person into the chamber 18 is pumped from the latter to the internal sections 2 and 3, so as to pass through the filters 4 and 5, and from the internal sections 2 and 3 it is pumped and expelled to the outside.

Consequently, while the pumped breath air passes through the filters 4 and 5, the analytes of interest contained in the breath air are retained by the stationary phase 16 included in the filters 4 and 5.

Successively, the officer opens and removes from the box 1 the respective cover 11, used for ensuring that the filters 4 and 5 had not been modified before the collection of the breath air sample.

Then a first one of the filters, for instance that indicated with 4, is extracted from the respective section 2 in the box 1 and checked by means of the BACT application kit 15, as schematized in FIG. 2.

If presence of road drugs was detected in the checking phase of this first filter 4, the box 1 is newly closed with the cover 11 and sent to a certified analysis laboratory.

In that place, after having checked that the cover 11 is intact so as to be sure that the second filter 5 has not been modified, the cover 11 is removed from the box 1 and also the second filter (5) is extracted from the respective section 3 in the box 1.

The second filter 5 is then analyzed by means of LC-MS/MS analysis in order to confirm the presence of road drugs in the checked person, as resulting by the check of the first filter 4.

Of course variants and improvements of the apparatus and method to sample and analyze volatile organic compounds in breath air, here described, can be envisaged, without departing from the scope of the present invention.

Moreover this apparatus and method have not to be considered as limited to sample and analyze road or street drugs, but their use and application can be extended to other fields, as clinical fields, and to environmental and food analysis.

The invention claimed is:

1. An apparatus or device (10, BACT) for use to sample and analyze volatile organic compounds (VOCS) in breath air, particularly suitable for performing road or street drug tests, wherein the apparatus is a portable sampling apparatus and comprises:
   a box (1) that is divided at the inside in two chambers or sections (2, 3), with each of said two sections (2, 3) housing a respective sample collecting filter (4, 5), in the form of a tube, containing a stationary phase (16) suitable for retaining determined analytes, as drugs and/or respective metabolites, having specific chemical or physical properties, contained in the breath air; and
   a breath pre-accumulation chamber (18) arranged for receiving a sample of breath air from the outside through a breath entrance connection (6) and for feeding the received breath air to the two sections (2, 3), housing the two sample collecting filters (4, 5) containing the stationary phase (16), with tubes (8, 21) being provided for connecting the pre-accumulation chamber (18) to the sample collecting filters (4, 5) housed in the two sections (2, 3), whereby a parallel connection is realized between said sample collecting filters (4, 5), and with the breath air moving from the pre-accumulation chamber (18) to the two sections (2, 3), while passing through the sample collecting filters (4, 5), whereby the analytes of interest in the air breath are retained by the stationary phase (16) contained in the sample collecting filters (4, 5), and moving from the two sections (2, 3) to the outside through respectively a first and a second expulsion connector (19, 20) in turn connected to a final breath expulsion connector (7);
   characterized by further comprising a tool application kit (15, 22, 23) for removing the two sample collecting filters (4, 5) from the respective sections (2, 3) in the box (1) of the apparatus (10), in a way that avoids any contamination of said sample collecting filters (4, 5), and for extracting the analytes that are retained by the stationary phase (16) on the same two sample collecting filters (4, 5),
   wherein said kit (15) is composed of a mechanical tool or instrument (22) suitable for removing the two sample collecting filters (4, 5) from the respective chamber or section (2, 3) in the box (1) of said apparatus (10), while avoiding to touch them with fingers and any other device that can lead to their contamination, and of an analyte extraction solution (23) suitable for extracting and solubilizing the analytes of interest retained by the stationary phase (16) in the two sample collecting filters (4, 5).

2. The apparatus of claim 1, wherein the breath air is moved from the
   pre-accumulation chamber (18) to the two sections (2, 3) and from the two sections (2, 3) to the outside by means of a pump (17).

3. The apparatus of claim 1, wherein the stationary phase (16) contained in said sample collecting filters (4, 5) is suitable for retaining different compounds depending on its composition, and wherein it is a reverse phase (Empore C 18 disk) to retain medium low polar compounds, or a cation exchange chromatographic resin suitable for retaining high polar compounds, or is composed both of a reverse phase and a cation exchange resin in order to retain both low polar and high polar compounds.

4. The apparatus of claim 1 wherein the two sections (2, 3) in which said box (1) is divided at its inside are each covered by a film (12, 13) that is provided for being removed only by an authorized officer.

5. The apparatus of claim 1 wherein the films (12, 13) covering said two sections (2, 3) can be of different materials, wherein said materials can be selected between aluminium and plastic.

6. The apparatus of claim 1, wherein said tool application kit (15, 23) is designed to prepare the samples, containing the analytes of interest extracted from said sample collecting filters (4, 5), so as to be suitable for being analyzed by means of a mass spectrometer.

7. The apparatus of claim 1, wherein said mechanical instrument (22) of said kit is designed for a single use and is closed in a plastic bag under sterile conditions before being used.

8. The apparatus of claim 1, wherein the solvent of said analyte extraction solution (23) of said kit is selected among H2O, H2O salts buffers, CH3CN, CH3OH or a mixture of these solvents, and wherein the solvent mixture is chosen between H2O salt buffer/CH3CN and H2O salt buffer/CH3OH.

9. The apparatus of claim 1, in combination with a mass spectrometry analyzer of the portable or non-portable type, wherein said analyte extraction solution (23) of said kit is intended to be analyzed by means of a said mass spectrometry analyzer of the portable or non-portable type, and wherein the mass spectrometry analyzer, when of the portable type, is used for detecting compounds in said analyte extraction solution (23) through full scan MS analysis.

10. The apparatus of claim 9, wherein,
    the mass spectrometry analyzer is the non-portable type, and
    after a positive detection of a drug in one of the two sample collecting filters (4, 5), the one of the two sample collecting filters (4) is removable in order to confirm said positive detection of the drug in the other of the two sample collecting filters (5).

11. The apparatus of claim 9, wherein the portable mass spectrometric analyzer can be selected between gas chromatography-mass spectrometer (GC-MS) and liquid chromatography-mass spectrometer (LC-MS).

12. A method for sampling and analyzing volatile organic compounds (VOCS) in breath air, particularly suitable for performing road or street drug tests from the police, by using a portable sampling apparatus or device comprising:
    a box (1) that is divided at the inside in two internal sections (2, 3), with each of said two internal sections (2, 3) housing a respective sample collecting filter (4, 5), in the form of a tube, containing a stationary phase (16) suitable for retaining determined analytes, as drugs and/or metabolites, having specific chemical physical properties, contained in the breath air;
    a breath pre-accumulation chamber (18) for receiving the breath air from the outside through a breath entrance connection (6) and for feeding the received breath air to the sample collecting filters (4, 5) housed in said two internal sections (2, 3), with these two sample collecting filters (4, 5) being connected in parallel to said pre-accumulation chamber (18); and
    a tool application kit (15, 22) for removing the two sample collecting filters (4, 5) from the box (1) of the apparatus (10) in a way that avoids any their contamination, wherein the method includes the following steps:
  emitting a sample of breath air into said pre-accumulation chamber (18);
  moving, by means of a pump (17), the breath air sample from the pre-accumulation chamber (18) to said two internal sections (2, 3) and from them (2, 3) to the outside, so that the analytes of interest contained in the breath air sample are retained, while the air breath passes through the two sample collecting filters (4, 5), by the stationary phase (16) contained in the tow sample collecting filters;
  successively removing, by means of said application kit (15, 22), at least a first one (4) of the two sample collecting filters (4, 5) from the apparatus in a way that avoids any contamination of it;
  extracting, from said first collecting filter (4), once removed, and by means of an analyte extraction solution (23) included in said application kit (15), the analytes of interest retained by the stationary phase (16) in said the first collecting filter (4); and
  analyzing the extracted analytes in order to detect the presence in them of drug and its metabolites;
wherein, in the event of a positive detection of drug and its metabolites in the extracted analytes and thereby in said first sample collecting filter (4), also the second filter (5) of said sample collecting filters (4, 5) is analyzed, by using a gas chromatography-mass spectrometer (GC-MS) of a liquid chromatography-mass spectrometer (LC-MS), in order to confirm the results of the analysis performed on the first sample collecting filter (4).

* * * * *